ns act as vectors to transfer DNA into fruit files".

United States Patent [19]

Narang et al.

[11] Patent Number: 4,830,965

[45] Date of Patent: May 16, 1989

[54] TRANSPOSABLE LINKERS TO TRANSFER GENETIC INFORMATION

[75] Inventors: Saran A. Narang, Nepean, Canada; John Goodchild, Worcester, Mass.; Ahmad I. Bukhari, deceased, late of Long Island, N.Y., by Christine K. Morgan, administratrix

[73] Assignees: Canadian Patents and Development Ltd., Ottawa, Canada; Cold Spring Harbor Laboratory, Cold Spring Harbor

[21] Appl. No.: 59,240

[22] Filed: Jun. 10, 1987

Related U.S. Application Data

[63] Continuation of Ser. No. 679,061, Dec. 6, 1984, abandoned.

[30] Foreign Application Priority Data

Dec. 12, 1983 [CA] Canada .................................. 443022

[51] Int. Cl.$^4$ ...................... C12N 15/00; C12P 21/00; C12P 19/34; C07H 21/04
[52] U.S. Cl. .................................. 435/172.3; 435/68; 435/91; 435/172.1; 435/320; 536/27; 935/6; 935/55; 935/56; 935/57; 935/58
[58] Field of Search .................. 435/68, 70, 71, 91, 435/172.1, 172.3, 235, 236, 320; 536/27; 935/6, 55–59

[56] References Cited

U.S. PATENT DOCUMENTS

| | | | |
|---|---|---|---|
| 4,336,336 | 6/1982 | Silhavy et al. | 435/91 |
| 4,358,477 | 9/1982 | Nakano et al. | 435/68 |
| 4,567,141 | 1/1986 | Olsen | 435/91 |
| 4,590,162 | 5/1986 | Grinter | 435/172.3 |

OTHER PUBLICATIONS

Van Gijsegem et al, "Chromosome transfer and R--prime formation by an RP4::mini-Mu derivative in *Escherichia coli, Salmonella typhimurium, Kleibsiella pneumoniae,* and *Proteus mirabilis*", Plasmid 7: 30 (1982).
Genetic Technology News, Nov. 1982, p. 6, "Transposons act as vectors to transfer DNA into fruit files".
Castilho et al, "Plasmid insertion mutagenesis and lac gene fusion with mini*mu bacteriphage transposons", J. Bacteriol. 158: 488 (1984).

*Primary Examiner*—James Martinell
*Attorney, Agent, or Firm*—Alan A. Thomson

[57] ABSTRACT

Transposable linkers are DNA sequences recognized and employed by transposition proteins, including transposases, in the insertion of genetic information into the genetic architecture of an organism and in the movement of genetic information from one location to another in the genetic architecture of an organism. Such linkers, comprising the extreme ends of transposons, often referred to as left and right attachment sites, have been isolated from the intervening material in transposons to produce a basic building block comprising simply the extreme ends of the transposons fused together. Using restriction endonuclease recognition sites outside and between the left and right attachment sites it is possible to introduce desired genes directly or via cloning vehicles, into the genetic material of an organism. A transposable linker may also be used to introduce a desired gene, that has been placed in a cloning vehicle but is not, of itself, part of a normally transposable sequence, into the genetic material of an organism.

9 Claims, No Drawings

TRANSPOSABLE LINKERS TO TRANSFER GENETIC INFORMATION

This application is a continuation of application Ser. No. 679,061, filed Dec. 6, 1984, now abandoned.

BACKGROUND TO THE INVENTION

Transposable genetic elements are specific DNA sequences that can move from one location to another on the host chromosome. In general, this transposition involves replication of the element (see: J. A. Shapiro, (ed), Mobile Genetic Elements, Academic Press, New York, 1983, for a review). It has become clear that this replication-transposition can have many genetic consequences, in that it can cause fusion of DNA molecules, dissociation of DNA segments, involving deletion formation, and inversion of DNA segments. Each of the DNA re-arrangements is accompanied by duplication of the element. It is also thought that the transposable elements can be inserted conservatively (without large scale replication) in some special cases. The elements can be excised at a low frequency, an event which leads to the loss of the element from a given site. In bacteriophage Mu, which is a virus as well as a transposon, this excision requires the activity of a specific protein, the transposase of Mu. Thus, the transposable elements are endowed with great potential to alter gene structure and genomes. They can re-arrange DNA structure at a local level or they can restructure a genome in a dramatic fashion.

The activity of transposable elements occurs through the action of specific proteins which recognize the ends of the element. If these proteins are not present, the element remains passive. When the transposition proteins are provided, the ends of the element are activated and invade different target sites, leading to transposition and other DNA re-arrangements. Thus, the nature and frequency of DNA re-arrangements in a cell can be controlled by regulating the activity of transposition proteins. Regulation of transposition would be fundamentally important for cells that have potentially active transposable genetic elements.

One protein that is absolutely necessary for transposition has been given the generic name "transposase". Highly active transposable elements, such as Mu, also use other specialized proteins that amplify the transposition process. The transposition proteins apparently bind to the ends of the element, and presumably to other proteins. This binding culminates in cleavage of DNA chains at the exact junction of the element and host DNA. In most prokaryotic transposable elements stuided so far, the end sequences are invertedly repeated, i.e. the same sequences are found in a reverse order at the left end and the right end. Bacteriophage Mu, although the most efficient transposon known, is an exception to this rule. Its two ends are not direct repeats of each other. In most other transposable elements, the inverted repeats are generally not perfect. For example, IS5, an insertion element found in Escherichia coli, has 16 base pairs of inverted repeats at the ends with one mismatch.

One approach to studying the mechanism of "end activation" by the transposase and other proteins is to synthesize specific polynucleotides and study their behaviour in vivo and in vitro. These polynucleotides, corresponding to the ends of the element to be studied, can be changed in a site-specific fashion. These studies then can help determine the features of the ends important to the transposition reaction.

A useful product would be the development of specialized transposons, using synthetic ends as "transposable linkers". These synthetic transposons could be useful tools in genetic engineering. For example, it should be possible to insert a cloned gene into any region of the host chromosome. The synthetic ends can be designed in a fashion that the inserted gene comes under the control of the host gene into which it is inserted.

SUMMARY OF THE INVENTION

This invention is concerned with DNA transposable linkers comprising a left attachment site and a right attachment site suitable for the insertion of foreign DNA into a chromosome. DNA sequences may comprise such transposable linkers. Such transposable linkers are recognized and employed by transposition proteins, such as transposases, to insert, delete or move genetic information in the genetic architecture of an organism but do not, of themselves, code for a complete set of transposition proteins. The DNA sequence may comprise, in the following order, (a) a left attachment site, (b) a gene sequence coding for a desired non-bacteriophage protein, and (c) a right attachment site. The DNA sequence may be preceded by at least one restriction endonuclease recognition site and be followed by at least one restriction endonuclease site. The DNA sequence further may have at least one restriction endonuclease recognition site, different from restriction endonuclease recognition sites that may precede and follow the attachment sites, positioned between the two attachment sites.

The DNA sequence may possess two restriction endonuclease recognition sites, recognized by the same restriction endonuclease and different from restriction endonuclease recognition sites that may be present elsewhere in the DNA sequence, placed at each end of a gene sequence, and positioned, with the gene sequence, between two attachment sites. The gene sequence may include a promoter and may be selected from such genes as human insulin, human proinsulin, somatostatin, animal growth hormone, and interferon. A method of constructing such a DNA sequence, including a gene sequence between the attachment sites, comprises (a) subjecting a DNA sequence, containing at least one restriction endonuclease recognition site positioned between the two attachment sites, to such a restriction endonuclease to open up the DNA sequence, and (b) ligating a DNA sequence comprising at least a gene sequence and a restriction endonuclease recognition site, recognized by the restriction endonuclease employed in step (a), into the product of step (a) to produce such a DNA sequence incorporating a gene sequence and two restriction endonuclease recognition sites between the attachment sites.

The above-mentioned DNA sequences may be incorporated into cloning vehicles and such a cloning vehicle may contain at least one gene sequence coding for a desired protein. The DNA sequence may be incorporated into a cloning vehicle, said cloning vehicle containing at least one gene sequence coding for a desired protein wherein said gene sequence may be the same as the gene sequence contained within the DNA sequence.

These DNA sequences may be incorporated into a chromosome and may also be incorporated into a non-human organism cell.

DETAILED DESCRIPTION OF THE INVENTION

This invention is particularly concerned with DNA sequences comprising, in the following order, (a) a restriction endonuclease recognition site, (b) 10-400 base pairs of the left end of a bacteriophage genome of sufficient size and with suitable nucleotide sequences to function as a left attachment site, (c) a restriction endonuclease recognition site different from (a) and (e), (d) about 10-400 base pairs of the right end of a bacteriophage genome of sufficient size and with suitable nucleotide sequences to function as a right attachment site, and (e) a restriction endonuclease recognition site. The DNA sequence may, for example, comprise (a) a Hind III restriction endonuclease recognition site, (b) a left attachment site of 101 base pairs of the left end of a Mu bacteriophage genome, (c) a Bgl II restriction endonuclease recognition site, (d) a right attachment site of 116 base pairs of the right end of a Mu bacteriophage genome, and (e) a Hind III restriction endonuclease recognition site.

DNA sequences, of the type herein described, may be inserted into genetic material of an organism by (a) subjecting the DNA sequence to transposition proteins that recognize the attachment sites, and (b) reacting the genetic material of an organism with the product of step (a) to insert the DNA sequence into the genetic material of an organism.

A DNA sequence-cloning vehicle composite, of the type herein described, may be inserted into the genetic material of an organism by (a) subjecting the DNA sequence-cloning vehicle composite to transposition proteins that recognize the attachment sites, and (b) reacting the genetic material of an organism with the product of step (a) to insert the DNA sequence-cloning vehicle composite into the genetic material of an organism.

In the methods, described above, of introducing DNA sequences and DNA sequence-cloning vehicle composites, the transposition proteins may be provided by the coincident introduction of a suitable bacteriophage. For example, in cases where the transposable linker subunits are derived from Mu bacteriophage, the coincident introduction of the Mu bacteriophage may be employed to provide transposition proteins.

DEFINITIONS

Attachment sites - Short sequences of DNA found at the left and right ends of the genome of a bacteriophage such as Mu and D108. The sequences are usually of the order of 10 to about 400 base pairs long and are recognized and employed by transposition proteins, such as transposases, to effect transposition. They do not, themselves, code for complete sets of transposition proteins. Each transposon contains two attachment sites, a left attachment site (called att.L.) and a right attachment site (att.R.).

Transposable linker—A sequence of DNA comprising at least a left attachment site and a right attachment site.

EXAMPLE 1

Construction of a Hind III-Mu att.L.-Bgl II-Mu att.R.-EcoRI DNA sequence (a) Rationale for chemical synthesis of the attachment sites To study the interaction of the end sequences with the transposase and to develop synthetic transposons, we chose to chemically synthesize the ends of bacteriophage Mu DNA. The reason for this choice is that Mu transposition is highly efficient and Mu undergoes about 100 events of transposition during its normal lytic cycle. However, when the A protein, the transposase, is absent Mu DNA remains totally inactive. Thus, transposition of Mu can be precisely controlled. We also synthesized 16 base pair (bp) inverted repeats of IS5. This experiment was designed to ask the question whether or not 16 bp at the ends of IS5 are sufficient for transposition and whether one base pair mismatch plays any role in the transposition reaction. One difficulty in studying elements such as IS5 is that we have no way for controlling their transposition activity, which to begin with, occurs at a very low level. One has to rely upon the transposase produced by the elements residing in the chromosome, and the synthesis of transposase may be sporadic in such cases. In addition, it is suspected that the transposase in many cases acts preferentially in Cis. Thus, the low level of the transposase produced may not "activate" the synthetic ends at a detectable frequency.

Our strategy for developing a synthetic Mu transposon was to chemically synthesize 101 base pairs from the left end of Mu and 116 base pairs from the right end of Mu and put them together in their natural orientation to each other, sandwiched by restriction endonuclease sites and sandwiching another restriction endonuclease site. We chose to synthesize 101 base pairs from the left end because recent studies have shown that they may contain all the signals necessary for Mu transposition. This inference was based on a comparative study of Mu and D108. D108 is a Mu-like phage and indeed its DNA is almost completely homologous to Mu without the exception of three regions of non-homology. We have determined the nucleotide sequence of the left end of D108 and compared it to Mu. These results show that the first 96 base pairs in Mu and D108 are the same, except for a change in one sequence, GATCTGAT in Mu, to TATTGGC in D108, beginning at bp 53 from the left end. From the nucleotide 96 onwards, there are many interspersed changes that continue until the base pair 251, after which the sequences of Mu and D108 completely diverge. Thus, the all important sequences probably lie within the first 10 bp. The change beginning at 53 bp is consistent with the observation that there is a slight difference in the specificity of the Mu and D108 transposase. Based on this consideration, we have inferred that the sequence from position 53-60 defines a site that is recognized by the transposase. The number of nucleotide chosen for the right end synthesis is 116, because it has been found that these 116 bp are sufficient for Mu transposition (see: A. Toussaint and A. Resibois in Mobile Genetic Elements, op.cit., 1983). The base pair sequences of the left and right ends (attachment sites) are given in R. Kahmann and D. Kamp, Nature, 280, 247-250, 1979, with one base pair error.

(b) Synthesis and Cloning of Mu Attachment Sites

The 101 base pairs from the left end were synthesized according to the sequence reported by H. Priess et al (Mol. Gen. Genet., 186, 315-321, 1982).

The chemical synthesis of the 37 individual deoxyribo-oligonucleotide fragments comprising the sequence of Mu left end 100 bp and Mu right end 116 bp was achieved by the solution modified phosphotriester method of S. A. Narang et al, 1980. These fragments were first assembled into a modular unit for left end Mu sequence and joined to give a dimeric palindrome sequence having Hind III restriction site at the termini and Bgl II at the center. The phophorylated left end Mu dimer fragment of 208 bp was then ligated with Hind III digestive pUC9 plasmid. The ligation mixture was used to transform competent E. coli HB101 cells. About 250 transformants were screened with a 32p label 24-mer (a part of left end Mu) hybrization probe. Three strongly hybridizing colonies were picked up for further study. The DNA sequence analysis by dideoxy method showed that none of the three had the intact dimer. Clone pNG83-3 has the complete monomer insert having Hind III and Bgl II at the termini whereas clone pNG83-37 had intact Hind III but Bgl II mutagenized.

The right end Mu DNA was assembled as a monomer containing Bgl II and EcoRI restriction sites at the termini and ligated to BamHIEcoRI fragment of pUC9. The ligation mixture was used to transform competent E. coli HB101 cells as described above.

(c) Biological Activity

We have tested the activity of the synthetic 101 bp left end of Mu. We have found that these 101 bp compete with Mu during the lytic cycle. When the plasmid containing the 101 bp was introduced into a strain containing a temperature-inducible prophage, the induction of the prophage was affected. The lytic cycle became sluggish, although the bacterial culture eventually lysed. However, the plaque-forming titers of the lysates were reduced more than 100-fold as compared to strains not containing the plasmid with the left end (Table 1). Thus, the 101 bp from the left end may be competing for the Mu transposase. The synthetic left end appears to undergo transposition at a low frequency. The transposition properties of the left end is being further examined and will be compared with the synthetic mini-Mu, containing the left end and the right end in their proper orientation. A kanamycin resistance gene has been cloned within the synthetic ends, so that transposition can be followed readily.

TABLE 1

| | Effect of the synthetic left end on the lytic cycle of Mu | |
|---|---|---|
| Strain | Plasmid | PFU/ml |
| 40-Mucts62 | pC9 | $1 \times 10^7$ |
| 40-Mucts62 | pD2 | $2 \times 10^7$ |
| 40-Mucts62 | — | $5 \times 10^9$ | pC9 and pD2 were constructed by cloning the synthetic 101 base pairs of Mu in pUC9 such that two copies of the left end are present in inverted orientation. Strain 40 is an E. coli K12 strain with the genotype Δprolac, trp-8, Str. Bacterial cultures were grown at 32° C. in Tryptoneyeast extract broth and were shifted to 42° C. at a density of $3 \times 10^8$ cells/ml for prophage induction. Cultures containing the plasmids lysed within 60 min. The supernatant of the cultures were assayed for plaque-forming units (PFU).

EXAMPLE 2

Synthetic DNA containing the Bacteriophage Mu packaging signal

The first 101 bp of the left end of bacteriophage Mu were chemically synthesized and cloned in to a pUC9 plasmid vector to give plasmid pNG83-36 following similar procedures to those given in Example 1. Both pNG83-36 and pUC9 plasmids carry an intact ampicillin resistance gene (Ap) which was used as a genetic marker. This pNG83-36 plasmid was then used to transform a lysogen of Mucts 62 (using pUC9 in control experiments). Phage lysates were then prepared from the resulting strains by heat induction and these lysates subsequently concentrated and used to infect Ap$^s$ recipients. Ap$^r$ transductants were selected on ampicillin containing plates. The Ap$^r$ transducing frequency of lysates prepared from cells containing pNG83-36 was at least 6200 times as high as the Ap$^r$ transducing frequency of lysates made from cells containing pUC9 (see table 2), suggesting that the plasmid containing the 101 bp synthetic DNA sequence of the left end can be efficiently packed into Mu phage heads. Plasmids extracted from colonies of the Ap$^r$ transduced cells by the alkaline lysis method (described in T. Maniatis et al, Molecular Cloning, Cold Spring Harbor Lab., 1982) were electrophoresed on 0.7% agarose gel. All preparations showed multiple bands which migrate with or more slowly than the pUC9 plasmid. In all cases on digestion with enzymes which cut the plasmid once (Hind III or Bgl II), a single band migrating with linear pNG83-36 was observed and it was deduced that the Ap$^r$ transductants contained monomeric and multimeric copies of pNG83-36.

To see if plasmid transduction is a recA-dependent process, the experiments were performed using recA$^-$ and recA$^+$ donor and recipient strains.

Lysogens were grown in LBCaMg broth and then induced, lysed and concentrated. The phage particles were resuspended in Mu buffer containing 0.2M Tris-HCl, pH 7.5, 0.2M NaCl, 1 mM CaCl$_2$, 20 mM MgSO$_4$ and 0.1% gelatin. The suspensions were used for titration and for transduction assay.

Approximately $10^{10}$ cells were mixed with phage lysates to achieve multiplicity of infection about 0.3 in 10 ml LB CaMg broth. The mixtures were incubated at 37° C. for 45 min and then 20 ml of 0.85% NaCl were added. These suspensions were centrifuged and the pellet resuspended in 1 ml of 0.85% NaCl. The infected cells were diluted in 0.85% NaCl solution and spread onto LB ampicillin (100 μg/ml) plates. The plates were incubated 48 hr at 32° C. Only a few Ap$^r$ transdutants could be obtained if the plates were incubated at 42° C. instead of 32° C.

TABLE 2

| Plasmid transduction using recA$^+$ and recA$^-$ donors and recipients | | |
|---|---|---|
| Donor cell recA$^+$ | Recipient cell recA$^-$ | Ratio of Transduction pNG83-36/pUC9 |
| + | + | 6200 |
| + | − | 1400 |
| − | + | 30 |

It can be seen from table 2 that when both the donor and the recipient are recA$^+$, the transduction frequency is high; at least 6200-fold higher than the pUC9 control. Since only a few stable Ap$^r$ transductants were obtained when pUC9 transduction was attempted, this is a minimum value. There is approximately a 4-fold reduction in the transduction frequency when the recipient carries a recA mutation, and a 200-fold reduction when the donor carried a recA mutation. Very few Ap$^r$ transductants were obtained when recA$^-$ donor and recipient were used. These results indicated that at least one mechanism of plasmid transduction is recA-dependent.

To verify that the plasmid pNG83-36 was integrated into the Mu genome, the phage particles derived from the recA+ and recA− donor cells containing pNG83-36 were purified and extracted. The phage DNA was electrophoresed on an agarose gel and then transferred to nitrocellulose membrane for hybridization studies. Plasmid pUC9 was used as a hybridizing probe. The phage DNA prepared from recA+ strain showed a much stronger hybridization to Mu DNA than from recA$^{31}$ strain. Negative controls consisting of Mu phage grown on strain HM8305 (without plasmid) were employed. With the recA+ strain, pUC9 hybridized to the Mu genome was expected because this could occur by homologous recombination between the 101 bp of the synthetic c-end in the plasmid pNG83-36 and c-end of prophage Mu. The pUC9 also hybridized to the Mu DNA isolated from the recA− strain and this is not yet understood. However, electron microscopy studies of DNA prepared from cells containing mini-Mu plasmids as well as full size Mu prophages have revealed structures in which circular plasmids are firmly attached to, although not cointegrated with, large DNA molecules. Both phage DNA isolated from recA+ and recA− strains also showed positive hybridization corresponding to multimeric and nicked plasmid positions. In contrast to the Mu DNA-hybridization bands, phage DNA prepared from recA− strain showed stronger hybridizing bands in the dimeric and nicked plasmid positions. When the phage DNA prepared from recA+ strain were cut with either Hind III or Bgl II, the Mu DNA-hybridized bands disappeared and concomitantly increased the intensity in the positions of the nicked plasmids. These results again suggested that the plasmid pNG83-36 was integrated into the Mu genome in the presence of recA+ system. On the other hand, the hybridization pattern of phage DNA prepared from recA$^{31}$ cells was unchanged with Hind III digestion. However, with Bgl II digestion some reduction of intensity in the Mu DNA and multimeric position were also observed, although there was no increasing intensity in the nicked plasmid band.

This most plausible pathway of plasmid transduction involves integration of the left end of the phage into the plasmid and integration of the resulting hybrid into the Mu genome. Integration of pNG83-36 into Mu DNA could occur by recombination between the 101 bp synthetic sequence in the plasmid and the homologous sequence at the extreme left end of Mu. This recombination event would result in a duplication of the 101 bp segment which would then flank the remaining plasmid sequences. If the Mu packaging signal is present in the duplicated 101 bp segment, then two signals are now present in the Mu DNA. If the innermost signal is utilized or if the packaging signal lies outside of the leftmost 101 bp then a packaging cut would be made somewhere within the plasmid sequences, since mature Mu DNA carries only 50-100 bp of host DNA on its left end. Consequently, the packaged phage DNA would not be able to transduce ampicillin resistance. On the other hand, if the outermost 101 bp carries the packaging signal, utilization of this signal would result in a phage DNA molecule carrying an insertion of about 2.8 kb in length. Upon injection of this DNA into the recipient, recombination could occur between the duplicated 101 bp segments thereby regenerating the plasmid. Since we do recover plasmid transductants at high frequency, this would indicate that the synthetic sequence does indeed carry the Mu packaging signal.

This mechanism is consistent with the requirement for a recA+ donor and recipient for the highest transduction frequencies (Table 2), since recombination would be required in the donor for integration of the plasmid into the phage DNA and in the recipient for regeneration of the plasmid. Furthermore, the hybridization and the restriction enzyme digestion of the purified phage DNA studies demonstrated that the transduction of the plasmid pNG83-86 occurred by integration of the plasmid into the Mu genome. The cointegrate indeed existed in the phage DNA prepared from the recA$^{30}$ strain.

This work has been verified using kanamycin resistance as a genetic marker instead of ampicillin resistance. Similar results have been obtained.

Example 2 demonstrates that elements of the Mu system can be used to transfer genetic information and that the genetic information can be integrated into the genetic material of a recipient cell. However, it is preferable only to employ components of the system (the elements of the transposable linker) which allow the insertion of foreign genetic material but do not allow the subsequent removal of such foreign genetic material (except when desired by the genetic engineer). Thus, transposable linkers acting in conjunction with appropriate transposition enzymes are to be preferred over the combination of an attachment site and a gene of choice together with the Mu bacteriophage already incorporated into the genome of a recipient cell. Ongoing work of this type is described below in Example 3.

EXAMPLE 3

Insertion of human insulin gene within a transposable linker and subsequent insertion into the genome of an organism The chemical synthesis of the synthetic ends of Mu clearly facilitates the studies of the mechanism of DNA transposition. The tools are at hand to manipulate the first 101 bp from the left end at will. We can rearrange these sequences in any fashion we want.

To develop the methodology for the "transposon linkers", we are cloning the human insulin gene within the synthetic Mu ends. In order to achieve this, the following procedure is being followed.

We are employing the transposable linker resulting from Example 1, comprising, in order, (a) a Hind III restriction endonuclease recognition site, (b) 101 base pairs of the left end of a Mu bacteriophage genome, (c) a Bgl II restriction endonuclease recognition site, (d) 116 pairs of the right end of a Mu bacteriophage genome, and (e) an EcoRI restriction endonuclease recognition site, opening up the linker at the Bgl II restriction endonuclease recognition site using Bgl II restriction endonuclease, inserting an insulin gene with oligonucleotide linkers and a second Bgl II restriction endonuclease recognition site and with or without a promoter and a genetic marker gene such as kanamycin or ampicillin resistance (these are a matter of choice) and closing the transposable linker to yield a modified transposable linker comprising (a), (b), (d) and (e) as before, and (c) a first Bgl II restriction endonuclease recognition site, a human insulin gene and a second Bgl II restriction endonuclease recognition site.

When provided with the Mu transposase, for example, from a helper Mu phage, the "synthetic insulin transposon" should insert into different genes of *E. coli*. The expression of the insulin gene may come under the control of a specific bacterial gene. This insertion into a host gene will stabilize the insulin gene, thus overcoming the problems associated with the loss of, or deletions, in plasmids containing the cloned insulin gene. These problems can be encountered as industrial scale up is attempted. Furthermore, it may be desirable in some cases to synthesize proteins such as insulin under the influence of different bacterial promoters.

We envision that the most important use of synthetic transposons would be manipulation of eukaryotic genes in vitro. The manipulated genes can be put back into the eukaryotic genomes. As an example, it is desirable to put the synthetic insulin gene under the control of an appropriate gene in mammalian cells. The "synthetic insulin transposon" can then be mixed with the cloned mammalian gene in an in vitro transposition system. The insulin gene will then insert different sites into the target gene and an appropriate insertion can then be chosen for further study. This would eliminate the cumbersome use of restriction enzymes for such work. The restriction enzyme recognition sites put several constraints on such constructions.

We claim:

1. A DNA sequence comprising, in the following order, (a) a Hind III restriction endonuclease recognition site, (b) a left attachment site of 101 base pairs of the left end of Mu bacteriophage genome, (c) a Bgl II restriction endonuclease recognition site, (d) a right attachment site of 116 base pairs of the right end of a Mu bacteriophage genome, and (e) a Hind III restriction endonuclease recognition site.

2. The DNA sequence of claim 1 wherein two Bgl II restriction endonuclease recognition sites are placed at each end of a gene sequence, and are positioned along with the gene sequence, between the two attachment sites at the location of recognition site (c).

3. The DNA sequence of claim 2 in which the gene sequence comprises a promoter.

4. The DNA sequence of claim 2 wherein the gene sequence is selected from the group consisting of genes that code for human insulin, human proinsulin, somatostatin, animal growth hormone, and interferon.

5. The DNA sequence of claim 2 incorporated into a cloning vehicle.

6. The DNA sequence of claim 2 incorporated into a cloning vehicle, said cloning vehicle containing at least one gene sequence coding for a desired protein.

7. A method of inserting a desired DNA sequence into genetic material of an organism comprising:
(i) providing a DNA transposable linker sequence comprising, in the following order, (a) a restriction endonuclease recognition site, (b) about 10–400 base pairs of the left end of a bacteriophage genome suitable to function as a left attachment site, (c) a restriction endonuclease recognition site different from (a), (d) about 10–400 base pairs of the right end of a bacteriophage genome suitable to function as a right attachment site, and (e) a restriction endonuclease recognition site different from (c);
(ii) incorporating the desired DNA sequence, having at each end the same recognition sites as said recognition site (c), into said transposible linker at said recognition site (c), to produce a desired DNA-linker composite;
(iii) introducing the desired DNA-linker composite and a selected bacteriophage which is capable of providing transposition proteins which recognize said attachment sites (b) and (d), into the presence of the genetic material of an organism, and
(iv) effecting transposition of the desired DNA-linker composite into the genetic material.

8. The method of claim 7 wherein step (ii) further comprises introducing the desired DNA-linker composite into a cloning vehicle, and step (iii) comprises introducing the cloning vehicle produced in step (ii) and a selected bacteriophage which is capable of providing transposition proteins which recognize said attachment sites (b) and (d), into the presence of the genetic material of an organism.

9. The method of claim 7, wherein the transposable linker sequence of (i) comprises, in the following order, (a) a Hind III restriction endonuclease recognition site, (b) a left attachment site of 101 base pairs of the left end of a Mu bacteriophage genome, (c) a Bgl II restriction endonuclease recognition site, (d) a right attachment site of 116 base pairs of the right end of a Mu bacteriophage genome, and (e) a Hind III restriction endonuclease recognition site.

* * * * *